(12) United States Patent
Pearce, III et al.

(10) Patent No.: US 12,336,507 B2
(45) Date of Patent: Jun. 24, 2025

(54) DIAPERS FOR NON-HUMANS INCLUDING SECTIONED ABSORBENT CORE

(71) Applicant: Manna Pro Products, LLC, Chesterfield, MO (US)

(72) Inventors: Robert C. Pearce, III, Chesterfield, MO (US); Scott Allan Plasek, Chesterfield, MO (US); Pi-Gi Brite, Chesterfield, MO (US)

(73) Assignee: Manna Pro Products, LLC, Chesterfield, MO (US)

( * ) Notice: Subject to any disclaimer, the term of this patent is extended or adjusted under 35 U.S.C. 154(b) by 858 days.

(21) Appl. No.: 17/602,671

(22) PCT Filed: Apr. 9, 2020

(86) PCT No.: PCT/US2020/027479
§ 371 (c)(1),
(2) Date: Oct. 8, 2021

(87) PCT Pub. No.: WO2020/210499
PCT Pub. Date: Oct. 15, 2020

(65) Prior Publication Data
US 2022/0174910 A1 Jun. 9, 2022

Related U.S. Application Data

(60) Provisional application No. 62/832,615, filed on Apr. 11, 2019.

(51) Int. Cl.
*A01K 23/00* (2006.01)
*A61F 13/15* (2006.01)
(Continued)

(52) U.S. Cl.
CPC ........ *A01K 23/00* (2013.01); *A61F 13/15739* (2013.01); *A61F 13/49058* (2013.01);
(Continued)

(58) Field of Classification Search
CPC .......... A01K 23/00; A61F 2013/15186; A61F 2013/530562; A61F 13/49058; A61F 13/49473; A61F 2013/4909; A61F 13/535
See application file for complete search history.

(56) References Cited

U.S. PATENT DOCUMENTS

| 6,837,191 B2 | 1/2005 | Brewington |
| 2005/0034687 A1 | 2/2005 | Solomon |

(Continued)

FOREIGN PATENT DOCUMENTS

| EP | 2441418 A1 | 4/2012 |
| JP | 2009131510 A | 6/2009 |

(Continued)

OTHER PUBLICATIONS

International Search Report and Written Opinion, dated Jun. 8, 2020, for PCT/US2020/027479 (17 pgs).

*Primary Examiner* — Susan S Su
(74) *Attorney, Agent, or Firm* — Husch Blackwell LLP

(57) ABSTRACT

An absorbent core for a diaper for a non-human has a total superabsorbent polymer (SAP) load. The absorbent core includes a first zone including a first absorbent section and a second absorbent section, a second zone including a third absorbent section, and a third zone including a fourth absorbent section and a fifth absorbent section. The absorbent sections each include a range of 15% to 20% of the total SAP load. The second zone is between the first zone and the third zone. The absorbent core further includes seals surrounding each of the first absorbent section, the second absorbent section, the third absorbent section, the fourth absorbent section, and the fifth absorbent section. One of the seals extends through the first zone between the first absorbent section and the second absorbent section, and another (Continued)

of the seals extends through the third zone between the fourth absorbent section and the fifth absorbent section.

18 Claims, 6 Drawing Sheets

(51) Int. Cl.
  *A61F 13/49* (2006.01)
  *A61F 13/494* (2006.01)
(52) U.S. Cl.
  CPC ............... *A61F 13/49473* (2013.01); *A61F 2013/15186* (2013.01); *A61F 2013/4909* (2013.01)

(56) References Cited

U.S. PATENT DOCUMENTS

| | | | |
|---|---|---|---|
| 2010/0319633 A1 | 12/2010 | Moncheski | |
| 2014/0076246 A1* | 3/2014 | Komatsubara | A01K 23/00 |
| | | | 119/869 |
| 2014/0276511 A1* | 9/2014 | Bauduin | A61F 13/15699 |
| | | | 604/365 |
| 2014/0371700 A1 | 12/2014 | Patel et al. | |
| 2015/0148766 A1* | 5/2015 | Nakakado | B29C 65/7894 |
| | | | 156/580.2 |
| 2015/0173980 A1* | 6/2015 | Umebayshi | B29C 66/234 |
| | | | 156/60 |
| 2015/0305308 A1* | 10/2015 | Komatsubara | A01K 23/00 |
| | | | 119/868 |
| 2018/0140477 A1 | 5/2018 | Minoguchi et al. | |
| 2018/0249681 A1 | 9/2018 | Martin | |
| 2018/0271064 A1 | 9/2018 | Komatsubara et al. | |
| 2018/0303682 A1 | 10/2018 | Nebigil | |

FOREIGN PATENT DOCUMENTS

| | | |
|---|---|---|
| TW | 201302173 A | 1/2013 |
| WO | 2012132460 A1 | 10/2012 |
| WO | 2017221472 A1 | 12/2017 |
| WO | 2018210751 A1 | 11/2018 |
| WO | 2019038451 A1 | 2/2019 |

* cited by examiner

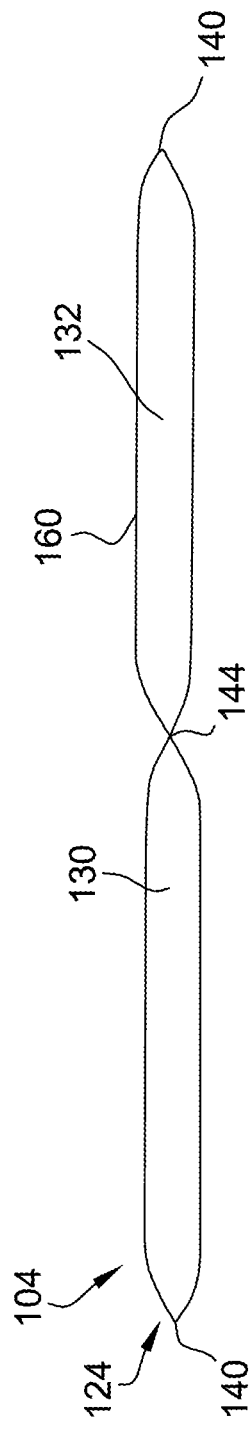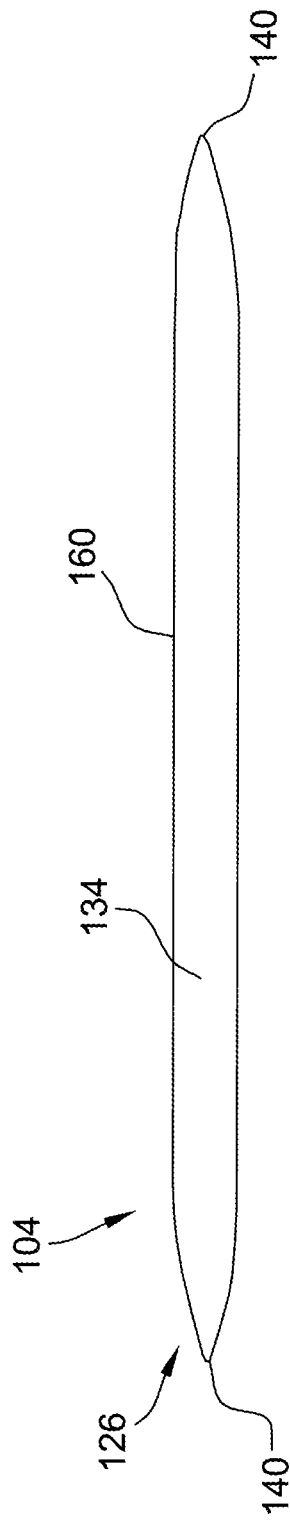

DIAPERS FOR NON-HUMANS INCLUDING SECTIONED ABSORBENT CORE

CROSS-REFERENCE TO RELATED APPLICATIONS

This application is a U.S. National Stage Application of International Patent Application No. PCT/US2020/027479, filed Apr. 9, 2020, which claims priority to U.S. Provisional Patent Application No. 62/832,615, filed Apr. 11, 2019, each of which is hereby incorporated by reference herein in their entirety.

FIELD OF THE DISCLOSURE

The disclosure is directed to diapers for non-humans and, more specifically, to diapers including sectioned absorbent cores arranged to accommodate non-humans.

BACKGROUND OF THE DISCLOSURE

Diapers are configured to contain body waste products or excreta including solids and fluids. Typical diapers are designed for human bodies and provide functionality and comfort when worn on the human body. For example, the diapers are configured to accommodate movement of human bodies, which move in a vertical, or upright, manner. The diapers also collect excreta that are typically released from the human body in a vertical manner, i.e., in a direction parallel to the legs of the human when the human is upright. However, non-humans, such as canines or felines, may also require diapers and the diapers designed for humans may not accommodate non-humans. For example, many non-humans are adapted to move in a four-legged horizontal manner. Four-legged non-humans typically release excreta from horizontal positions, not vertical positions like from humans. Diapers that are designed to contain excreta released in a vertical direction may not properly contain excreta that is released from a non-human in a horizontal direction.

In addition, humans' legs extend vertically in a direction parallel to the body and rotate approximately 180° at the hips. As such, human legs are generally circular in cross-section to accommodate the 180° rotation. In contrast, many non-humans have legs that extend downward in a direction perpendicular to the horizontal body of the non-humans and rotate approximately 90° at the hips relative to the body. Accordingly, the non-humans' legs may be other than circular (e.g., elliptical) to accommodate the 90° rotation. However, most diapers are designed to fit humans and include, for example, circular leg openings. When applied to diapers for non-humans, the circular leg openings may result in gaps between the legs of the non-human that allow excreta to leak around the legs. In addition, the absorbent material of diapers designed for humans may not properly receive and contain excreta from non-humans.

Accordingly, there is a need for a disposable diaper that is adapted specifically for non-humans, such as canines or felines, and that provides enhanced functionality and comfort when worn by the non-humans.

BRIEF DESCRIPTION OF THE DISCLOSURE

In one aspect, an absorbent core for a diaper for a non-human has a total superabsorbent polymer (SAP) load and includes a first zone including a first absorbent section and a second absorbent section. The first absorbent section and the second absorbent section each include a range of 15% to 20% of the total SAP load. The absorbent core also includes a second zone including a third absorbent section including a range of 15% to 20% of the total SAP load and a third zone including a fourth absorbent section and a fifth absorbent section. The first absorbent section and the second absorbent section each include 2 a range of 15% to 0% of the total SAP load. The second zone is between the first zone and the third zone. The absorbent core further includes seals surrounding each of the first absorbent section, the second absorbent section, the third absorbent section, the fourth absorbent section, and the fifth absorbent section. One of the seals extends through the first zone between the first absorbent section and the second absorbent section, and another of the seals extends through the third zone between the fourth absorbent section and the fifth absorbent section.

In another aspect, a diaper for a non-human includes a chassis configured to form two leg openings when the diaper is placed on a non-human in a wear configuration. The diaper also includes an absorbent core attached to the chassis. The absorbent core includes at least five absorbent sections and a plurality of seals separating the absorbent sections from each other. Each absorbent section includes a superabsorbent polymer (SAP) material that is a range of 15% to 20% of a total SAP load of the diaper. At least two of the absorbent sections extend along each leg opening. The leg openings have an elliptical shape when the diaper is placed on the non-human in the wear configuration.

In yet another aspect, a method of making an absorbent core for a diaper for a nonhuman includes depositing a superabsorbent polymer in zones of the absorbent core to form a total superabsorbent polymer (SAP) load of the absorbent core. The absorbent core includes a first zone including a first absorbent section and a second absorbent section. The first absorbent section and the second absorbent section each include a range of 15% to 20% of the total SAP load. The absorbent core also includes a second zone including a third absorbent section including a range of 15% to 20% of the total SAP load and a third zone including a fourth absorbent section and a fifth absorbent section. The first absorbent section and the second absorbent section each include a range of 15% to 20% of the total SAP load. The second zone is between the first zone and the third zone. The method further includes forming seals around the first absorbent section, the second absorbent section, the third absorbent section, the fourth absorbent section, and the fifth absorbent section. One of the seals extends through the first zone between the first absorbent section and the second absorbent section. Another of the seals extends through the third zone between the fourth absorbent section and the fifth absorbent section.

BRIEF DESCRIPTION OF THE DRAWINGS

The embodiments described herein may be better understood by referring to the following description in conjunction with the accompanying drawings.

FIG. 3 is a cross-sectional view of an absorbent core of the diaper shown in FIG. 1 taken along line 3-3.

FIG. 4 is a cross-sectional view of an absorbent core of the diaper shown in FIG. 1 taken along line 4-4.

DETAILED DESCRIPTION OF THE DISCLOSURE

Embodiments of a diaper for a non-human include an absorbent core having at least five absorbent sections. The diaper also includes a chassis including a front edge, a back edge, and sides extending between the front and back edges. The absorbent core is attached to the chassis and positioned to absorb excreta of a non-human wearer. The sections of the absorbent core extend perpendicular to the waistband of the diaper. For example, at least one middle section extends through the middle of the diaper along the length of the diaper. At least two first side sections having approximately equal length are positioned end-to-end on a left side of the middle section. At least two second side sections having approximately equal length are positioned end-to-end on a right side of the middle section. The absorbent sections are separated by seals. Due at least partially to the arrangement of the sections of the absorbent core, the diaper forms leg openings that are non-circular in shape and accommodate the legs of non-human species to provide an improved function and fit of the diaper for non-humans.

In addition, the absorbent core includes a superabsorbent polymer (SAP). Each absorbent section is filled with a range of 15% to 20% of a total SAP load of the diaper. Thus, the first side sections provide a range of 30% to 40% of the total SAP load, the middle section provides a range of 20% to 40% of the total SAP load, and the second side sections provide a range of 30% to 40% of the total SAP load. As a result, the absorbent core allows for an initial release of excreta to be absorbed by the a range of 20% to 40% SAP in the middle section and any remaining excreta is absorbed by a range of 30% to 40% SAP in the first side sections and the second side sections to prevent leakage out the diaper around the non-human's leg.

Figure 1:
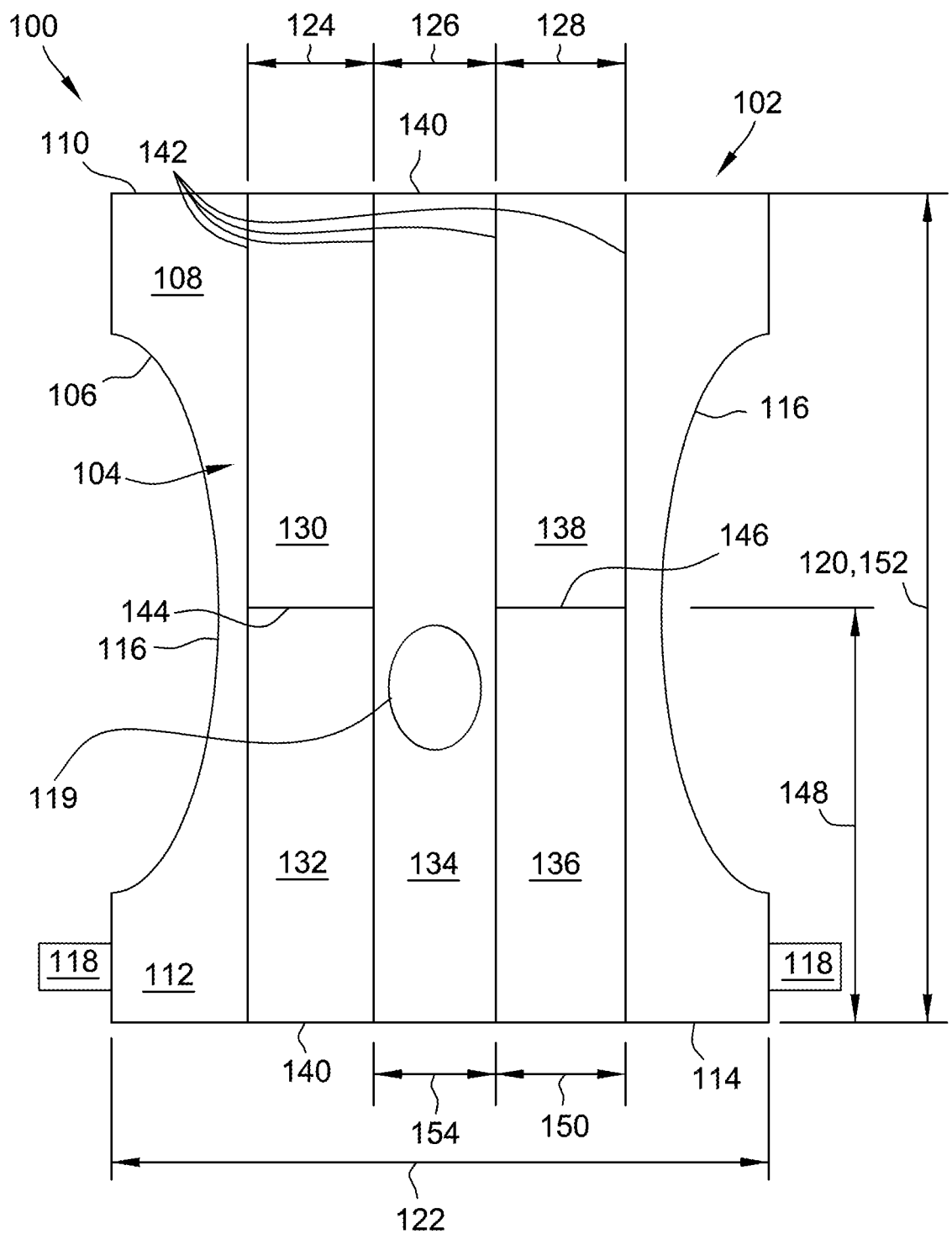
FIG. 1 is a top view of a diaper for a non-human in a laid-flat configuration.

FIG. 1 is a top view of an exemplary embodiment of an absorbent article in the form of a diaper, generally indicated at 100, for a non-human. The diaper 100 includes a chassis 102 and an absorbent core 104 attached to the chassis. For example, in some embodiments, the absorbent core 104 is positioned between an inner sheet and an outer sheet 106 of the chassis 102 in a sandwiched configuration. The absorbent core 104 may be adhered, bonded, entrapped, or otherwise attached to the chassis 102. In some embodiments, the absorbent core 104 forms a portion of the chassis 102 such as the inner layer. In such embodiments, the absorbent core 104 may directly contact the body of the wearer. In other embodiments, an inner sheet extends between the absorbent core 104 and the body and is at least semi-permeable to allow excreta to pass through the inner sheet and reach the absorbent core.

The chassis 102 includes a front 108 having a front edge 110, a back 112 having a back edge 114, and sides 116 extending between the front edge and the back edge. When the diaper 100 is in a wear configuration, the front 108 and the back 112 attach together to form a waistband that is sized and shaped to extend around the wearer. For example, the chassis 102 may include fasteners 118 that secure the front 108 and the back 112 together. The fasteners 118 may include hook and loop fasteners, adhesives, and/or any other suitable fasteners. The fasteners 118 may be formed as part of or attached to the front 108 and/or the back 112. For example, in the illustrated embodiment, the fasteners 118 extend from the back 112 and attach to the material of the front 108 when the diaper is in the wear configuration.

Figure 6:
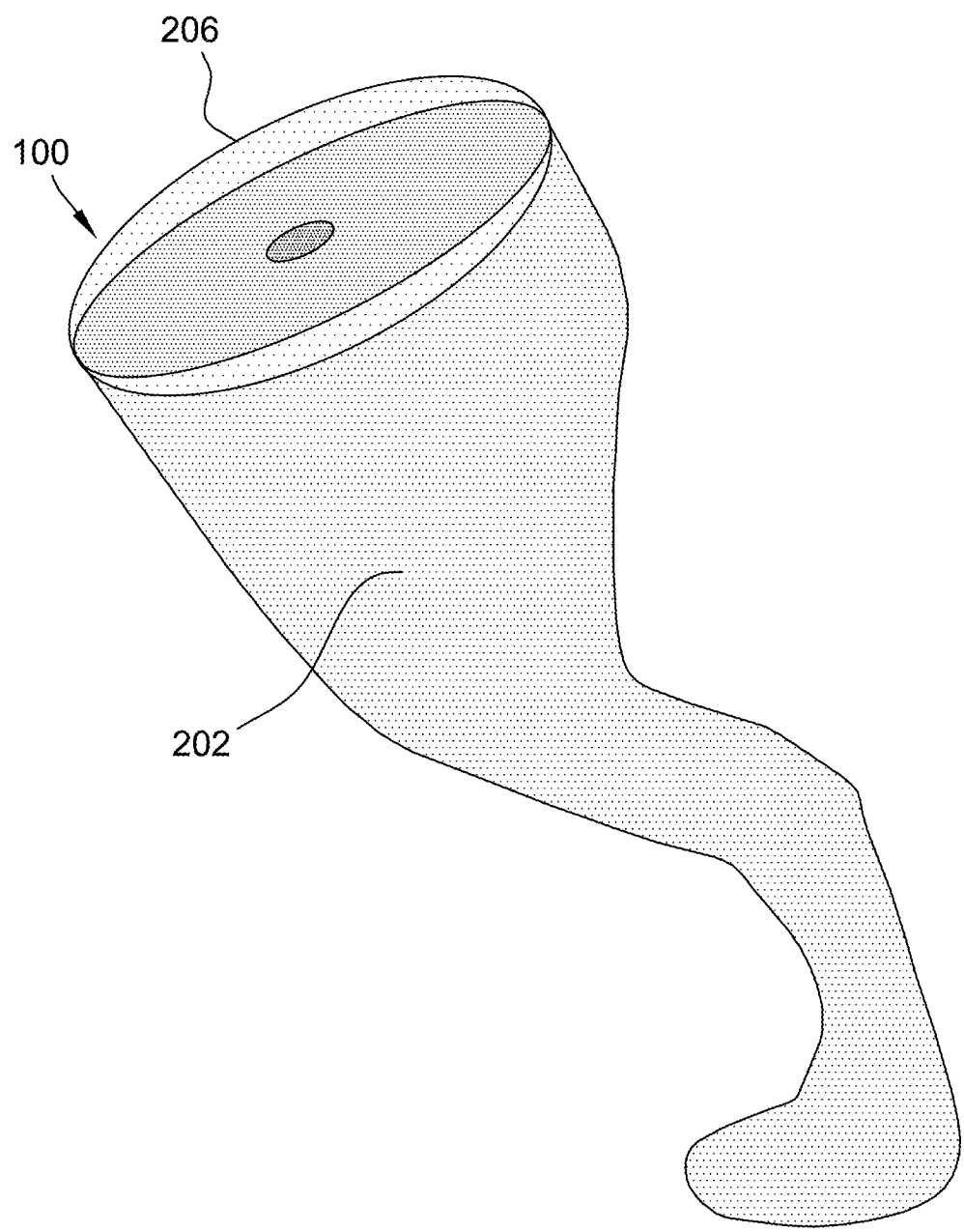
FIG. 6 is a schematic perspective view illustrating the fit of the diaper shown in FIG. 1 on a leg of a non-human.

In addition, the sides 116 form leg openings that accommodate the legs of the wearer when the diaper 100 is in the wear configuration. The sides 116 may be curved (e.g., concave) as shown in the illustrated embodiment. As described further herein, the diaper 100 is adapted to accommodate noncircular legs of non-humans. Specifically, the configuration of the chassis 102 and the absorbent core 104 allow the diaper to conform to the shape of non-humans. For example, as shown in FIG. 6, a leg opening of the diaper 100 conforms to the shape of a leg 202 of a non-human such as a canine or a feline and forms a tight seal around the leg to prevent leakage. In addition, the diaper 100 includes an opening 119 in the middle of the diaper sized and shaped to accommodate a tail of a non-human.

The chassis 102 has a length 120 defined between the front edge 110 and the back edge 114. Also, the chassis 102 has a width 122 defined between the sides 116. The chassis 102 may be sized to accommodate bodies of non-humans. For example, in some embodiments, the length 120 may be in a range of about 98 centimeters (cm) to about 142 cm and the width 122 may be in a range of about 110 cm to about 172 cm.

The absorbent core 104 is attached to the chassis 102 between the front edge 110 and the back edge 114 and extends along the length 120 of the chassis. The absorbent core 104 includes a first absorbent zone 124, a second absorbent zone 126, and a third absorbent zone 128. The second absorbent zone 126 extends along a centerline of the chassis 102. The first absorbent zone 124 and the third absorbent zone 128 are on opposite sides of the second absorbent zone 126 between the second absorbent zone and respective sides 116 of the chassis 102. Accordingly, the second absorbent zone 126 is configured to receive excreta that is released into a central region of the diaper 100 and the first absorbent zone 124 and the third absorbent zone 128 provide a secondary receiving area to seal along the sides 116 and prevent any excreta not absorbed by the second absorbent zone 126 from flowing out of the diaper 100 along the sides 116.

The absorbent core 104 includes a plurality of sections that are arranged in the zones 124, 126, 128 to absorb the excreta released by the non-human wearer. For example, the first absorbent zone 124 includes a first absorbent section 130 and a second absorbent section 132. The second absorbent zone 126 includes a third absorbent section 134. The third absorbent zone 128 includes a fourth absorbent section 136 and a fifth absorbent section 138. Accordingly, in the illustrated embodiment, the absorbent core 104 includes at least five absorbent sections. In other embodiments, the absorbent core may include any suitable absorbent sections. For example, in some embodiments, the first absorbent zone 124 and the third absorbent zone 128 each include three or more absorbent sections. In further embodiments, the second absorbent zone 126 includes two or more absorbent sections.

The absorbent sections 130, 132, 134, 136, 138 of the absorbent zones 124, 126, 128 are bounded by seals 140, 142, 144, 146. For example, the absorbent core 104 includes edge seals 140 that extend parallel to the front edge 110 and the back edge 114 of the chassis 102 on opposite ends of the absorbent zones 124, 126, 128 and along the ends of the absorbent sections 130, 132, 134, 136, 138. Also, the absorbent core 104 includes longitudinal seals 142 that extend longitudinally between the absorbent zones 124, 126, 128 and along the sides of the absorbent sections 130, 132, 134, 136, 138. In addition, the absorbent core 104 includes a first lateral seal 144 that extends through the first absorbent zone 124 between the first absorbent section 130 and the second absorbent section 132. The absorbent core 104 includes a second lateral seal 146 that extends through the third absorbent zone between the fourth absorbent section 136 and the fifth absorbent section 138. The lateral seals 144, 146 extend perpendicular to the longitudinal seals 142 and parallel to the front edge 110 and the back edge 114 of the chassis 102. The seals 140, 142, 144, 146 overlap and connect to each other. As a result, each absorbent section 130, 132, 134, 136, 138 is completely encircled by the seals 140, 142, 144, 146 and each absorbent section 130, 132, 134, 136, 138 acts as an individual absorbent body to absorb excreta and the sections 130, 132, 134, 136, 138 are able to move relative to each other.

The seals 140, 142, 144, 146 may be formed in any suitable manner. For example, the seals 140, 142, 144, 146 may be heat seals that are formed by heating layers of the absorbent core 104. In some embodiments, the seals may be formed by ultrasonic bonding, welding, and any other suitable process. For example, in some embodiments, the absorbent sections 130, 132, 134, 136, 138 may be separated by embossments formed using embossing rollers.

The first absorbent section 130, the second absorbent section 132, the fourth absorbent section 136, and the fifth absorbent section 138 are identical to each other and each have a length 148 and a width 150. The length 148 is greater than the width 150 and is equal to approximately half of the total length of the absorbent core 104. The third absorbent section 134 is a different size from the first absorbent section 130, the second absorbent section 132, the fourth absorbent section 136, and the fifth absorbent section 138. The third absorbent section 134 has a length 152 and a width 154. The length 152 is approximately equal to the total length of the absorbent core 104. The width 154 of the third absorbent section 134 equal to the width 150 of the first absorbent section 130, the second absorbent section 132, the fourth absorbent section 136, and the fifth absorbent section 138 such that a ratio of each width 150, 154 to the total width of the absorbent core 104 is 1:3.

Figure 2:
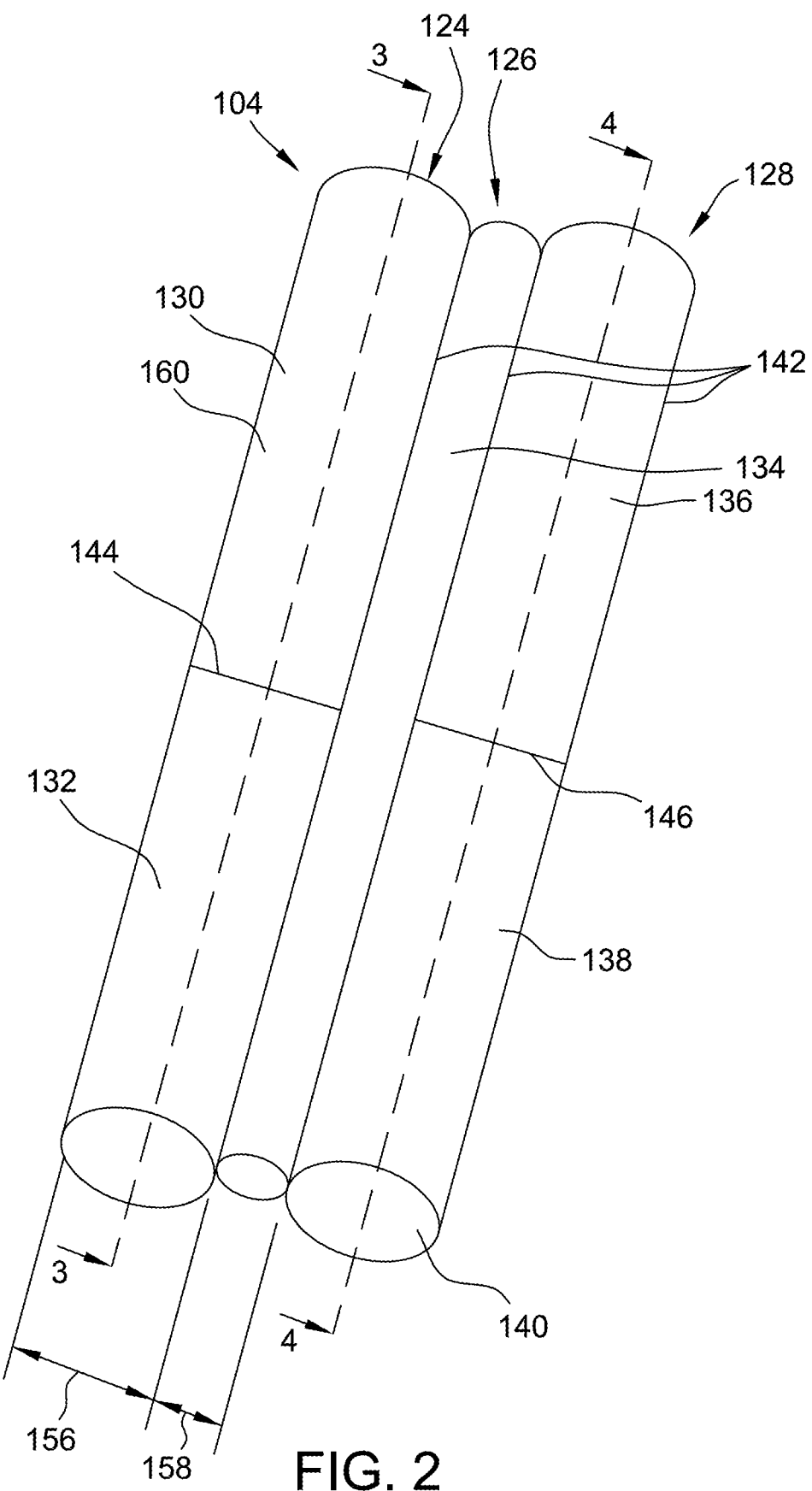
FIG. 2 is a perspective view of an absorbent core of the diaper shown in FIG. 1.

FIG. 2 is a perspective view of the absorbent core 104 of the diaper 100 (shown in FIG. 1). The absorbent core 104 may include any absorbent material that is configured to absorb excreta. For example, the absorbent core 104 may be constructed of a superabsorbent polymer (SAP). The SAP may be distributed throughout the absorbent core 104 in an arrangement that accommodates a non-human wearer. For example, the first absorbent section 130, the second absorbent section 132, the third absorbent section 134, the fourth absorbent section 136, and the fifth absorbent section 138 each include a range of 15% to 20% of the total SAP load. Accordingly, the first absorbent zone 124 and the third absorbent zone 128 each include a range of 30% to 40% of the total SAP load of the absorbent core 104. The second absorbent zone 126 includes a range of 15% to 20% of the total SAP load of the absorbent core 104. In other embodiments, the second absorbent zone 126 includes a range of 20% to 40% of the total SAP load of the absorbent core 104. The SAP in the second absorbent zone 126 is distributed along the length of the absorbent core 104 in the center region and is configured to absorb excreta released by a non-human in a horizontal direction. The first absorbent zone 124 and the third absorbent zone 128 are configured to absorb excreta that is not absorbed by the second absorbent zone 126 to prevent the excreta from flowing toward the sides 116 (shown in FIG. 1) of the diaper 100.

When the SAP absorbs excreta, as shown in FIG. 2, each section 130, 132, 134, 136, 138 expands. In the illustrated embodiment, each section 130, 132, 134, 136, 138 forms a cylinder when the SAP within each section 130, 132, 134, 136, 138 is fully loaded. The first absorbent section 130, the second absorbent section 132, the fourth absorbent section 136, and the fifth absorbent section 138 are identical to each other and each have an expanded width 156 that is greater than the width 150. The third absorbent section 134 has an expanded width 158 that is less than the expanded width 156 of the first absorbent section 130, the second absorbent section 132, the fourth absorbent section 136, and the fifth absorbent section 138. Accordingly, when the SAP has absorbed fluids, the third absorbent section 134 has an elongate, thinner shape in comparison to the first absorbent section 130, the second absorbent section 132, the fourth absorbent section 136, and the fifth absorbent section 138.

FIG. 3 is a cross-sectional view of the absorbent core 104 of the diaper 100 taken along line 3-3. Line 3-3 extends through the first absorbent zone 124. The absorbent zone 124 includes the first absorbent section 130 and the second absorbent section 132 which are separated by the seal 144. The seal 144 extends through a middle of the first absorbent zone 124 such that the first absorbent section 130 and the second absorbent section 132 are approximately equal halves of the first absorbent zone 124. The first absorbent zone is symmetric about the seal 144. The seal 144 defines a minimum thickness of the first absorbent zone 124 (i.e., a thickness substantially less than the thickness of the first absorbent section 130 and the second absorbent section 132) and separates the sections from each other. Accordingly, the first absorbent section 130 and the second absorbent section 132 are distinct absorbent regions and act as separate absorbent bodies to absorb excreta. Moreover, the seal 144 acts as a joint between the sections 130 and 132 and allows for movement of the sections relative to each other. As a result, the sections 130 and 132 may allow the leg openings of the diaper 100 (shown in FIG. 1) to assume an elliptical shape when the diaper is in the wear configuration. The foregoing description also applies to the third absorbent zone 128 because the third absorbent zone 128 is identical to the first absorbent zone 124 other than being positioned on an opposite side of the second absorbent zone 126.

FIG. 4 is a cross-sectional view of the absorbent core 104 of the diaper 100 taken along line 4-4. Line 4-4 extends through the second absorbent zone 126. The third absorbent section 134 extends throughout the entirety of the second absorbent zone 126. Accordingly, the second absorbent zone 126 is not divided by any seals and has a substantially uniform thickness. The third absorbent section 134 is positioned generally in a middle area of the diaper 100 (shown in FIG. 1) and is arranged to receive an initial discharge of excreta from the non-human wearer. The excreta may be distributed substantially evenly throughout the SAP of the third absorbent section 134 because of the uniform thickness of the third absorbent section 134.

Referring to FIGS. 1-4, a method of assembling the diaper 100 generally includes forming the chassis 102 and attaching the absorbent core 104 to the chassis 102. For example, the absorbent core 104 may be attached to the outer sheet 106 of the chassis 102 and/or sandwiched between two or more sheets 106 of the chassis. One or more sheets 106 may be secured together to form the chassis 102 before, after, or simultaneous with the absorbent core 104 being attached to the chassis.

The chassis 102 may be cut or formed to a shape including the front edge 110, the back edge 114, and/or the sides 116. In some embodiments, the sides 116 may be at least partially curved to accommodate the legs of the wearer. The fasteners 118 may be attached to or otherwise provided on the chassis 102 such that the diaper 100 has a laid flat configuration (shown in FIG. 1) and a wear configuration.

The absorbent core 104 may be formed of one or more sheets 160 that are arranged to receive the SAP. The SAP may be distributed and/or injected into the respective sections 130, 132, 134, 136, 138 of the absorbent core 104 in desired ratios. For example, each section 130, 132, 134, 136, 138 may receive about ⅕ of the total SAP for the absorbent core. Suitably, the seals 140, 142, 144, 146 are formed during the same manufacturing step that the SAP is positioned in the absorbent core 104 in an in-situ manufacturing process. In other embodiments, channels could be formed between and around the sections 130, 132, 134, 136, 138 using one or more embossing rollers.

The distribution of the SAP is closely controlled and the formation of the seals is more precise relative to the distribution of the SAP because the seals are formed during the distribution of the SAP. As a result, the amount of SAP required to assemble the diaper 100 is reduced and the efficiency of the manufacturing process is increased. In some embodiments, the edges and/or sides of the absorbent core 104 may be sealed after the SAP is distributed. In other embodiments, the SAP is distributed onto the sheet 160 before at least one of the seals 140, 142, 144, 146 is formed.

After the sealing process, the diaper 100 may undergo further processing such as printing and/or coating. In some embodiments, the diapers 100 are formed in continuous sheets and the diapers 100 are cut apart from each other before shipping. Each diaper 100 is then prepared for shipping. For example, each diaper 100 may be folded and packaged for shipping.

Figure 5:
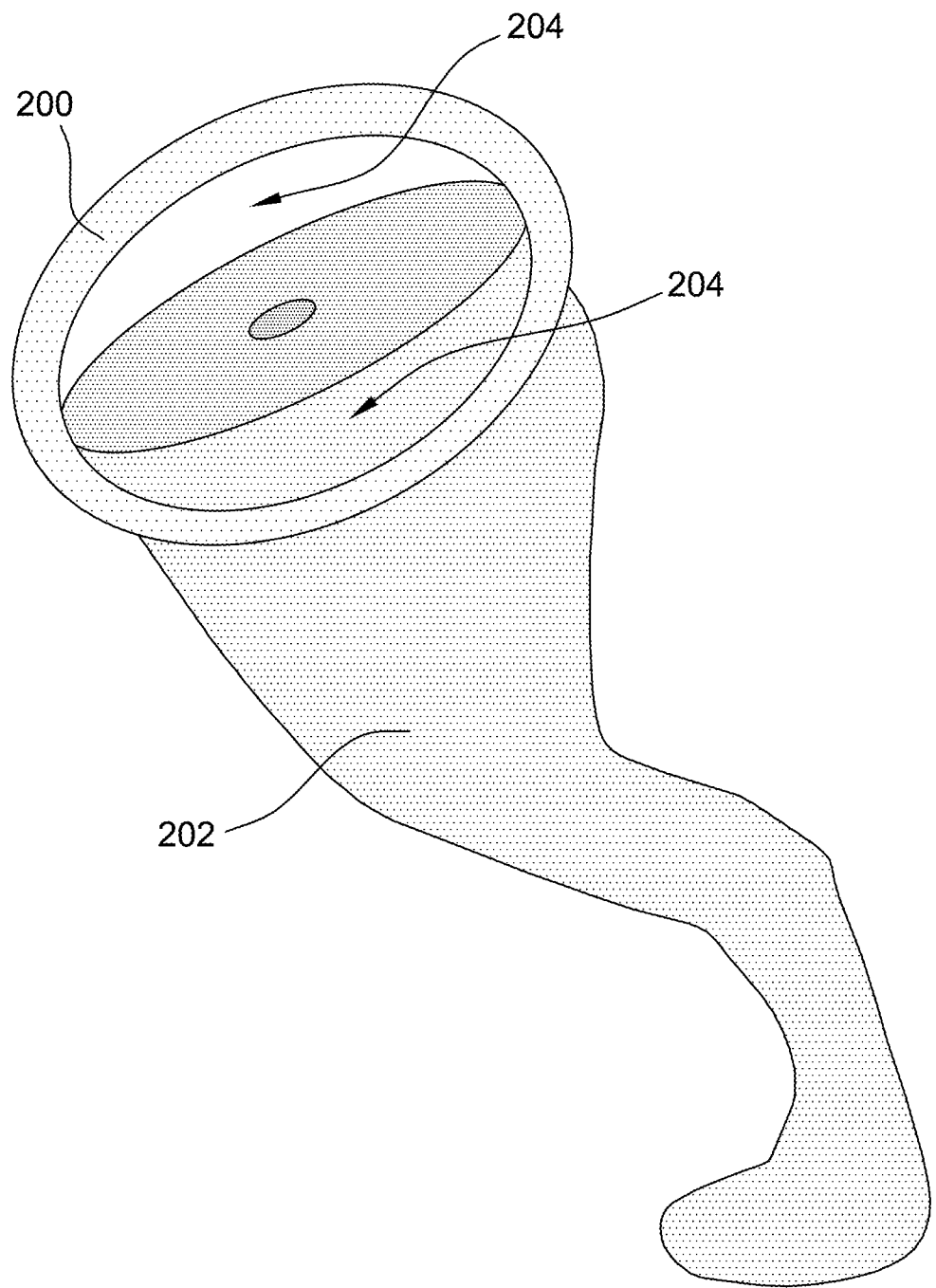
FIG. 5 is a schematic perspective view illustrating the fit of a diaper with a conventional leg opening on a leg of a non-human.

FIG. 5 is a schematic perspective view illustrating a diaper with a conventional leg opening 200 on a leg 202 of a non-human. The leg opening 200 forms a circular shape because of the arrangement of the absorbent core of the diaper. For example, the absorbent core around the leg opening is substantially continuous and provides a uniform bend or curve and causes the circular shape. The circular shape is configured to accommodate most human legs but does not conform to the shape of non-human legs. For example, the circular shape of the leg opening 200 forms gaps 204 around the leg 202 of the non-human because the leg 202 has a generally non-circular shape. Accordingly, the diaper may allow excreta to leak around the leg 202 through the gaps 204.

FIG. 6 is a schematic perspective view illustrating the diaper 100 on the leg 202 of the non-human. In contrast to the conventional diaper shown in FIG. 5, the diaper 100 fits snugly on the leg 202 and provides a tight seal to prevent leakage around the leg 202. For example, the arrangement of the absorbent sections 130, 132, 134, 136, 138 and the seals 146 allow the leg openings 206 to have an elliptical shape and accommodate the generally elliptical shape of the leg 202. In particular, the lateral seals 146 allow the absorbent core 104 to at least partially bend or crease at a midpoint of the absorbent core 104 and form the elliptical shape. Accordingly, the leg opening 206 and the absorbent core 104 conform to the shape of the leg 202 such that the diaper 100 prevents leaks and provides a more comfortable fit for the wearer.

Figure 7:
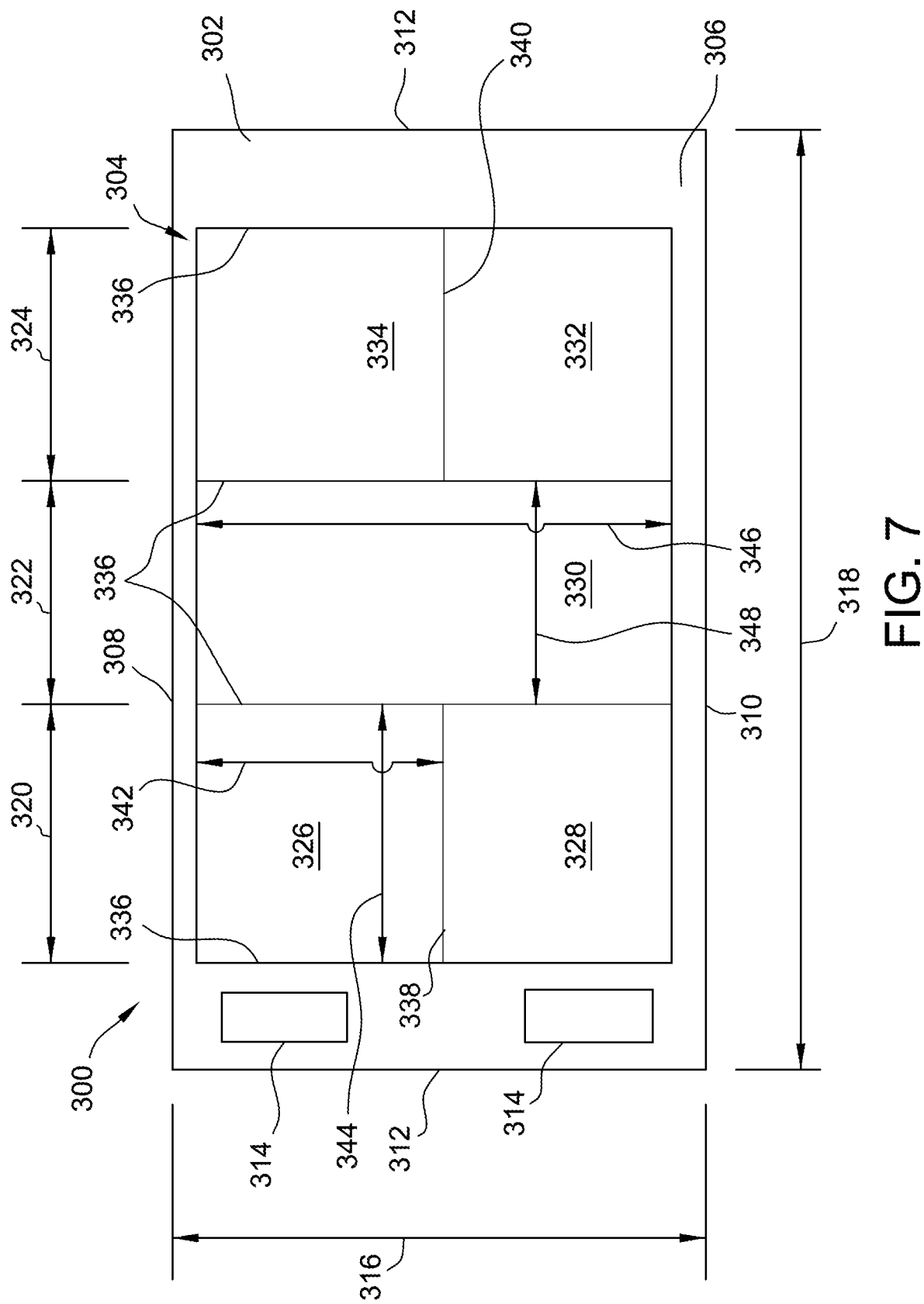
FIG. 7 is a top view of a diaper for a non-human in a laid flat configuration, the diaper is adapted for a male non-human.

FIG. 7 is a top view of another exemplary embodiment of an absorbent article in the form of a diaper, generally indicated at 300, for a non-human. The diaper 300 is configured, in particular, for use on a male non-human. For example, the diaper 300 may extend around the waste of the male non-human to collect urine released in a horizontal direction. In particular, the diaper 300 acts as a wrap that covers the inguinal region and/or the penis of the non-human to collect urine and other excreta that is emitted by the male non-human. The diaper 300 does not extend across the tail end of the non-human. In some embodiments, the diaper 300 may be used as a surgical wrap to cover a surgical site of a non-human.

The diaper 300 includes a chassis 302 and an absorbent core 304 attached to the chassis. For example in some embodiments, the absorbent core 304 is positioned between an inner sheet and an outer sheet 306 of the chassis 302 in a sandwiched configuration. The absorbent core 304 may be adhered, bonded, entrapped, or otherwise attached to the chassis 302. In some embodiments, the absorbent core 304 forms a portion of the chassis 302 such as the inner layer. In such embodiments, the absorbent core 304 may directly contact the body of the wearer. In other embodiments, an inner sheet extends between the absorbent core 304 and the body and is at least semi-permeable to allow excreta to pass through and reach the absorbent core.

The chassis 302 includes a front edge 308, a back edge 310, and sides 312 extending between the front edge and the back edge. The diaper 300 is sized and shaped to wrap around the wearer in a wear configuration and the sides 312 are configured to attach together to secure the diaper 300 in the wear configuration. For example, the chassis 302 may include one or more fasteners 314 that attach the sides 312 together. The fasteners 314 may include hook and loop fasteners, adhesives, and/or any other suitable fasteners. The fasteners 314 may be formed as part of or attached to the chassis 302. For example, in the illustrated embodiment, the fasteners 314 extend along one side 312 of the chassis and attach to another side 312 when the diaper 300 is in the wear configuration. In other embodiments, the diaper 300 may include a single fastener 314 extending along the side 312. In further embodiments, the diaper 300 includes one or more straps (not shown) that facilitate securing the diaper to the non-human.

The chassis 302 has a width 316 defined between the front edge 308 and the back edge 310. Also, the chassis 302 has a length 318 defined between the sides 312. Accordingly, the chassis 302 has a rectangular shape. In addition, the chassis 302 may be sized to accommodate bodies of non-humans. For example, in some embodiments, the width 316 may be in a range of about 270 cm to about 350 cm and the length 318 may be in a range of about 190 cm to about 400 cm.

The absorbent core 304 includes a first absorbent zone 320, a second absorbent zone 322, and a third absorbent zone 324. The second absorbent zone 322 extends along a centerline of the chassis 302. The first absorbent zone 320 and the third absorbent zone 324 extend between the second absorbent zone 322 and respective sides 312 of the chassis 302. The diaper 300 is configured to wrap around the non-human such that the second absorbent zone 322 is positioned along the inguinal region of the non-human and the first absorbent zone 320 and the third absorbent zone 324 are positioned at least partially along the sides of the non-human. Accordingly, the second absorbent zone 322 is configured to receive excreta that is released into a central region of the diaper 300 and the first absorbent zone 320 and the third absorbent zone 324 provide a secondary receiving area to seal along the sides 312 and prevent any excreta not absorbed by the second absorbent zone 322 from escaping the diaper.

The zones 320, 322, 324 include a plurality of absorbent sections 326, 328, 330, 332, 334 that are arranged to absorb excreta released by the non-human wearer. For example, the first absorbent zone 320 includes a first absorbent section 326 and a second absorbent section 328. The second absorbent zone 322 includes a third absorbent section 330. The third absorbent zone 324 includes a fourth absorbent section 332 and a fifth absorbent section 334. Accordingly, the absorbent core 304 includes at least five absorbent sections. In other embodiments, the absorbent core may include any suitable absorbent sections. For example, in some embodiments, the first absorbent zone 320 and the third absorbent zone 324 each include three or more absorbent sections. In further embodiments, the second absorbent zone 322 includes two or more absorbent sections.

The absorbent sections 326, 328, 330, 332, 334 may be any suitable shape. In the illustrated embodiment, the diaper 300 is configured to accommodate a male non-human such as a canine or a feline and the absorbent sections 326, 328, 330, 332, 334 are arranged to absorb excreta released by the male non-human. For example, the first absorbent section 326, the second absorbent section 328, the fourth absorbent section 332, and the fifth absorbent section 334 each are square. The third absorbent section 330 is a rectangle. The shapes of the absorbent sections 326, 328, 330, 332, 334 provide a desired distribution of the SAP and facilitate the diaper 300 being positioned around the waistline of the non-human.

The absorbent sections 326, 328, 330, 332, 334 of the absorbent core 304 are bounded by longitudinal seals 336 and lateral seals 338, 340. The longitudinal seals 336 extend along the width 316 of the chassis 302 between the front edge 308 and the back edge 310 of the chassis. In addition, the first absorbent section 326 and the second absorbent section 328 of the first absorbent zone 320 are separated by a first lateral seal 338. The fourth absorbent section 332 and the fifth absorbent section 334 are separated by a second lateral seal 340. The lateral seals 338, 340 extend perpendicular to the longitudinal seals 336 and parallel to the front edge 308 and the back edge 310 of the chassis 302. Accordingly, the seals 336, 338, 340 divide the absorbent zones 320, 322, 324 into the absorbent sections 326, 328, 330, 332, 334 and completely circumscribe each absorbent section 326, 328, 330, 332, 334.

The first absorbent section 326, the second absorbent section 328, the fourth absorbent section 332, and the fifth absorbent section 334 are identical to each other and each have a length 342 and a width 344. The length 342 is equal to the width 344 and is equal to approximately half of the total length of the absorbent core 304. The third absorbent section 330 is a different shape from the first absorbent section 326, the second absorbent section 328, the fourth absorbent section 332, and the fifth absorbent section 334. The third absorbent section 330 has a length 346 and a width 348. The length 346 is approximately equal to the total length of the absorbent core 304. The width 348 of the third absorbent section 330 is equal to the width 344 of the first absorbent section 326, the second absorbent section 328, the fourth absorbent section 332, and the fifth absorbent section 334 such that a ratio of each width 344, 348 to the total width of the absorbent core 304 is 1:3.

The SAP may be distributed throughout the absorbent core 304 in an arrangement that accommodates a non-human wearer. For example, the first absorbent section 326, the second absorbent section 328, the third absorbent section 330, the fourth absorbent section 332, and the fifth absorbent section 334 each include a range of 15% to 20% of the total SAP. Accordingly, the first absorbent zone 320 and the third absorbent zone 324 each include a range of 30% to 40% of the total SAP load of the absorbent core 304. The second absorbent zone 322 includes a range of 15% to 20% of the total SAP load of the absorbent core 304. The SAP in the second absorbent zone 322 is distributed along the length of the absorbent core 104 in the center region and is configured to absorb excreta released by a non-human in a horizontal direction. The first absorbent zone 320 and the third absorbent zone 324 are configured to absorb excreta that is not absorbed by the second absorbent zone 322.

As used herein, the terms "about," "substantially," "essentially," and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation.

When introducing elements of the present disclosure or the embodiment(s) thereof, the articles "a," "an," "the," and "said" are intended to mean that there are one or more of the elements. The terms "comprising," "including," "containing," and "having" are intended to be inclusive and mean there may be additional elements other than the listed elements. The use of terms indicating a particular orientation (e.g., "top," "bottom," "side," etc.) is for convenience of description and does not require any particular orientation of the item described.

As various changes could be made in the above constructions and methods without departing from the scope of the disclosure, it is intended that all matter contained in the above description and shown in the accompanying drawings shall be interpreted as illustrative and not in a limiting sense.

What is claimed is:

1. An absorbent core for a diaper for a non-human, the absorbent core having a total superabsorbent polymer (SAP) load and comprising:
   a first zone including a first absorbent section and a second absorbent section, wherein the first absorbent section and the second absorbent section each include a range of 15% to 20% of the total SAP load;
   a second zone including a third absorbent section including a range of 15% to 20% of the total SAP load;
   a third zone including a fourth absorbent section and a fifth absorbent section, wherein the fourth absorbent section and the fifth absorbent section each include a range of 15% to 20% of the total SAP load, and wherein the second zone is between the first zone and the third zone; and
   seals surrounding each of the first absorbent section, the second absorbent section, the third absorbent section, the fourth absorbent section, and the fifth absorbent section, wherein one of the seals extends through the first zone between the first absorbent section and the second absorbent section, and another of the seals extends through the third zone between the fourth absorbent section and the fifth absorbent section;
   wherein each of the first, second, fourth, and fifth absorbent sections have a first width and a first length;

wherein the third absorbent section has a second width and a second length;

wherein the first width and the second width are substantially equal; and wherein the second length is greater than the first length.

2. The absorbent core of claim 1, wherein the first zone has a first zone width, the second zone has a second zone width, and the third zone has a third zone width, and wherein the first zone width is equal to the third zone width.

3. The absorbent core of claim 2, wherein the second zone width is equal to the first zone width.

4. The absorbent core of claim 1, wherein a ratio of the first length to the second length is 1:2.

5. The absorbent core of claim 1, wherein the seals comprise heat seals formed in an ultrasonic or heat welding process.

6. The absorbent core of claim 1, wherein the seals extending through the first zone and the third zone are lateral seals extending parallel to an edge of the absorbent core.

7. The absorbent core of claim 6, wherein the seals further include longitudinal seals extending perpendicular to the lateral seals and between the first zone and the second zone and between the second zone and the third zone.

8. A diaper for a non-human, the diaper comprising:
a chassis configured to form two leg openings when the diaper is placed on a non-human in a wear configuration; and
an absorbent core attached to the chassis and comprising at least five absorbent sections and a plurality of seals separating the absorbent sections from each other, wherein each absorbent section includes a superabsorbent polymer (SAP) material that is a range of 15% to 20% of a total SAP load of the diaper, at least two of the absorbent sections extending along each leg opening, wherein the leg openings have an elliptical shape when the diaper is placed on the non-human in the wear configuration;
wherein a first, second, fourth, and fifth absorbent section of the at least five absorbent sections each have a first width and a first length;
wherein a third absorbent section of the at least five absorbent sections has a second width and a second length;
wherein the first width and the second width are substantially equal; and
wherein the second length is greater than the first length.

9. The diaper of claim 8 wherein the absorbent sections are arranged in a first absorbent zone, a second absorbent zone, and a third absorbent zone, the first absorbent zone including the first absorbent section and the second absorbent section, the second absorbent zone is located between the first absorbent zone and the third absorbent zone and includes the third absorbent section, and the third absorbent zone including the fourth absorbent section and the fifth absorbent section.

10. The absorbent core of claim 9, wherein the first absorbent zone has a first zone width, the second absorbent zone has a second zone width, and the third absorbent zone has a third zone width, and wherein the first zone width, the second zone width, and the third zone width are equal.

11. The diaper of claim 9, wherein the seals include lateral seals extending through the first absorbent zone and the third absorbent zone and parallel to an edge of the absorbent core.

12. The diaper of claim 11, wherein the seals further include longitudinal seals extending perpendicular to the lateral seals and between the first absorbent zone and the second absorbent zone and between the second absorbent zone and the third absorbent zone.

13. The diaper of claim 9 where the non-human is a male canine or feline and each of the first, second, fourth, and fifth absorbent sections is square.

14. The diaper of claim 9 where the non-human is a female canine or feline and each of the first, second, third, fourth, and fifth absorbent sections is a rectangle.

15. A method of making an absorbent core for a diaper for a nonhuman, the method comprising:
depositing a superabsorbent polymer in zones of the absorbent core to form a total superabsorbent polymer (SAP) load of the absorbent core, wherein the zones include:
a first zone including a first absorbent section and a second absorbent section, wherein the first absorbent section and the second absorbent section each include a range of 15% to 20% of the total SAP load;
a second zone including a third absorbent section including a range of 15% to 20% of the total SAP load; and
a third zone including a fourth absorbent section and a fifth absorbent section, wherein the fourth absorbent section and the fifth absorbent section each include a range of 15% to 20% of the total SAP load, the second zone is between the first zone and the third zone; and
forming seals around the first absorbent section, the second absorbent section, the third absorbent section, the fourth absorbent section, and the fifth absorbent section, wherein one of the seals extends through the first zone between the first absorbent section and the second absorbent section and another of the seals extends through the third zone between the fourth absorbent section and the fifth absorbent section;
wherein each of the first, second, fourth, and fifth absorbent sections have a first width and a first length;
wherein the third absorbent section has a second width and a second length;
wherein the first width and the second width are substantially equal; and
wherein the second length is greater than the first length.

16. The method of claim 15, wherein sealing around the first absorbent section, the second absorbent section, the third absorbent section, the fourth absorbent section, and the fifth absorbent section comprises forming heat seals by delivering heat to one or more layers of the absorbent core.

17. The method of claim 15, wherein sealing around the first absorbent section, the second absorbent section, the third absorbent section, the fourth absorbent section, and the fifth absorbent section comprises forming laterals seals extending between the first absorbent section and the second absorbent section and between the fourth absorbent section and the fifth absorbent section.

18. The method of claim 17, wherein sealing around the first absorbent section, the second absorbent section, the third absorbent section, the fourth absorbent section, and the fifth absorbent section further comprises forming longitudinal seals extending perpendicular to the lateral seals on a perimeter of the first absorbent section, the second absorbent section, the third absorbent section, the fourth absorbent section, and the fifth absorbent section such that each of the first absorbent section, the second absorbent section, the third absorbent section, the fourth absorbent section, and the fifth absorbent section is a rectangle.

* * * * *